(12) United States Patent
Claude et al.

(10) Patent No.: US 7,776,926 B1
(45) Date of Patent: *Aug. 17, 2010

(54) BIOCOMPATIBLE COATING FOR IMPLANTABLE MEDICAL DEVICES

(75) Inventors: Charles D. Claude, Sunnyvale, CA (US); Syed F. A. Hossainy, Fremont, CA (US); Eugene T. Michal, San Francisco, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 772 days.

This patent is subject to a terminal disclaimer.

(21) Appl. No.: 10/317,435

(22) Filed: Dec. 11, 2002

(51) Int. Cl.
*A61K 47/30* (2006.01)
(52) U.S. Cl. .................. 514/772.1; 517/772; 517/772.3
(58) Field of Classification Search .................. None
See application file for complete search history.

(56) References Cited

U.S. PATENT DOCUMENTS

| | | |
|---|---|---|
| 2,072,303 A | 3/1937 | Herrmann et al. |
| 2,386,454 A | 10/1945 | Frosch et al. |
| 3,773,737 A | 11/1973 | Goodman et al. |
| 3,849,514 A | 11/1974 | Gray, Jr. et al. |
| 4,226,243 A | 10/1980 | Shalaby et al. |
| 4,329,383 A | 5/1982 | Joh |
| 4,343,931 A | 8/1982 | Barrows |
| 4,529,792 A | 7/1985 | Barrows |
| 4,611,051 A | 9/1986 | Hayes et al. |
| 4,656,242 A | 4/1987 | Swan et al. |
| 4,733,665 A | 3/1988 | Palmaz ..................... 128/343 |
| 4,800,882 A | 1/1989 | Gianturco .................. 128/343 |
| 4,882,168 A | 11/1989 | Casey et al. |
| 4,886,062 A | 12/1989 | Wiktor ..................... 128/343 |
| 4,931,287 A | 6/1990 | Bae et al. |
| 4,941,870 A | 7/1990 | Okada et al. |
| 4,977,901 A | 12/1990 | Ofstead ..................... 128/772 |
| 5,019,096 A | 5/1991 | Fox, Jr. et al. |
| 5,100,992 A | 3/1992 | Cohn et al. |
| 5,112,457 A | 5/1992 | Marchant .................... 204/165 |
| 5,133,742 A | 7/1992 | Pinchuk |
| 5,163,952 A | 11/1992 | Froix |
| 5,165,919 A | 11/1992 | Sasaki et al. |
| 5,219,980 A | 6/1993 | Swidler |
| 5,258,020 A | 11/1993 | Froix |
| 5,272,012 A | 12/1993 | Opolski |
| 5,292,516 A | 3/1994 | Viegas et al. |
| 5,298,260 A | 3/1994 | Viegas et al. |
| 5,300,295 A | 4/1994 | Viegas et al. |
| 5,306,501 A | 4/1994 | Viegas et al. |
| 5,306,786 A | 4/1994 | Moens et al. |
| 5,328,471 A | 7/1994 | Slepian ..................... 604/101 |
| 5,330,768 A | 7/1994 | Park et al. |
| 5,380,299 A | 1/1995 | Fearnot et al. |
| 5,417,981 A | 5/1995 | Endo et al. |
| 5,447,724 A | 9/1995 | Helmus et al. |
| 5,455,040 A | 10/1995 | Marchant .................... 424/426 |
| 5,462,990 A | 10/1995 | Hubbell et al. |
| 5,464,650 A | 11/1995 | Berg et al. .................. 427/2.3 |
| 5,485,496 A | 1/1996 | Lee et al. |
| 5,516,881 A | 5/1996 | Lee et al. |
| 5,569,463 A | 10/1996 | Helmus et al. |
| 5,578,073 A | 11/1996 | Haimovich et al. ............ 623/1 |
| 5,584,877 A | 12/1996 | Miyake et al. |
| 5,605,696 A | 2/1997 | Eury et al. .................. 424/423 |
| 5,607,467 A | 3/1997 | Froix |
| 5,609,629 A | 3/1997 | Fearnot et al. |
| 5,610,241 A | 3/1997 | Lee et al. |
| 5,616,338 A | 4/1997 | Fox, Jr. et al. |
| 5,624,411 A | 4/1997 | Tuch |
| 5,628,730 A | 5/1997 | Shapland et al. |
| 5,644,020 A | 7/1997 | Timmermann et al. |
| 5,649,977 A | 7/1997 | Campbell |
| 5,658,995 A | 8/1997 | Kohn et al. |
| 5,667,767 A | 9/1997 | Greff et al. .............. 424/9.411 |
| 5,670,558 A | 9/1997 | Onishi et al. ................ 523/112 |
| 5,674,242 A | 10/1997 | Phan et al. |
| 5,679,400 A | 10/1997 | Tuch |
| 5,700,286 A | 12/1997 | Tartaglia et al. ................ 623/1 |
| 5,702,754 A | 12/1997 | Zhong |
| 5,711,958 A | 1/1998 | Cohn et al. |
| 5,716,981 A | 2/1998 | Hunter et al. ............... 514/449 |
| 5,721,131 A | 2/1998 | Rudolph et al. |
| 5,723,219 A | 3/1998 | Kolluri et al. |
| 5,735,897 A | 4/1998 | Buirge |
| 5,746,998 A | 5/1998 | Torchilin et al. |
| 5,759,205 A | 6/1998 | Valentini |
| 5,776,184 A | 7/1998 | Tuch |

(Continued)

FOREIGN PATENT DOCUMENTS

DE    42 24 401    1/1994

(Continued)

OTHER PUBLICATIONS

"Stent". Medical Encyclopedia. Online. Acessed on Nov. 8, 2006. <http://www.nlm.nih.gov/medlineplus/print/ency/article/002303.htm>.*

(Continued)

*Primary Examiner*—Eric E. Silverman
(74) *Attorney, Agent, or Firm*—Squire Sanders & Dempsey, LLP

(57) ABSTRACT

A random or a block copolymer which includes at least one biologically compatible structural moiety and at least one biologically active moiety is disclosed. The random or block copolymer can be used for fabricating a coating for an implantable medical device such as a stent.

18 Claims, No Drawings

U.S. PATENT DOCUMENTS

| | | | |
|---|---|---|---|
| 5,783,657 A | 7/1998 | Pavlin et al. | |
| 5,788,979 A | 8/1998 | Alt et al. | |
| 5,800,392 A | 9/1998 | Racchini | |
| 5,820,917 A | 10/1998 | Tuch | |
| 5,824,048 A | 10/1998 | Tuch | |
| 5,824,049 A * | 10/1998 | Ragheb et al. | 623/1.44 |
| 5,830,178 A | 11/1998 | Jones et al. | 604/49 |
| 5,837,008 A | 11/1998 | Berg et al. | |
| 5,837,313 A | 11/1998 | Ding et al. | 427/2.21 |
| 5,849,859 A | 12/1998 | Acemoglu | |
| 5,851,508 A | 12/1998 | Greff et al. | 424/9.411 |
| 5,854,376 A | 12/1998 | Higashi | |
| 5,858,746 A | 1/1999 | Hubbell et al. | 435/177 |
| 5,865,814 A | 2/1999 | Tuch | 604/265 |
| 5,869,127 A | 2/1999 | Zhong | |
| 5,873,904 A | 2/1999 | Ragheb et al. | 623/1 |
| 5,876,433 A | 3/1999 | Lunn | |
| 5,877,224 A | 3/1999 | Brocchini et al. | |
| 5,879,713 A | 3/1999 | Roth et al. | |
| 5,902,875 A | 5/1999 | Roby et al. | |
| 5,905,168 A | 5/1999 | Dos Santos et al. | |
| 5,910,564 A | 6/1999 | Gruning et al. | |
| 5,914,387 A | 6/1999 | Roby et al. | |
| 5,919,893 A | 7/1999 | Roby et al. | |
| 5,925,720 A | 7/1999 | Kataoka et al. | |
| 5,932,299 A | 8/1999 | Katoot | |
| 5,955,509 A | 9/1999 | Webber et al. | |
| 5,958,385 A | 9/1999 | Tondeur et al. | |
| 5,962,138 A | 10/1999 | Kolluri et al. | |
| 5,964,794 A * | 10/1999 | Bolz et al. | 607/121 |
| 5,971,954 A | 10/1999 | Conway et al. | 604/96 |
| 5,980,928 A | 11/1999 | Terry | 424/427 |
| 5,980,972 A | 11/1999 | Ding | 427/2.24 |
| 5,997,517 A | 12/1999 | Whitbourne | |
| 6,010,530 A | 1/2000 | Goicoechea | |
| 6,011,125 A | 1/2000 | Lohmeijer et al. | |
| 6,015,541 A | 1/2000 | Greff et al. | 424/1.25 |
| 6,033,582 A | 3/2000 | Lee et al. | |
| 6,034,204 A | 3/2000 | Mohr et al. | |
| 6,042,875 A | 3/2000 | Ding et al. | 427/2.24 |
| 6,051,576 A | 4/2000 | Ashton et al. | |
| 6,051,648 A | 4/2000 | Rhee et al. | 525/54.1 |
| 6,054,553 A | 4/2000 | Groth et al. | |
| 6,056,993 A | 5/2000 | Leidner et al. | 427/2.25 |
| 6,060,451 A | 5/2000 | DiMaio et al. | 514/13 |
| 6,060,518 A | 5/2000 | Kabanov et al. | |
| 6,080,488 A | 6/2000 | Hostettler et al. | 428/423.3 |
| 6,096,070 A | 8/2000 | Ragheb et al. | 623/1 |
| 6,099,562 A | 8/2000 | Ding et al. | 623/1.46 |
| 6,110,188 A | 8/2000 | Narciso, Jr. | 606/153 |
| 6,110,483 A | 8/2000 | Whitbourne et al. | |
| 6,113,629 A | 9/2000 | Ken | 623/1.1 |
| 6,120,491 A | 9/2000 | Kohn et al. | |
| 6,120,536 A | 9/2000 | Ding et al. | 623/1.43 |
| 6,120,788 A | 9/2000 | Barrows | |
| 6,120,904 A | 9/2000 | Hostettler et al. | 428/423.3 |
| 6,121,027 A | 9/2000 | Clapper et al. | 435/180 |
| 6,129,761 A | 10/2000 | Hubbell | 623/11 |
| 6,136,333 A | 10/2000 | Cohn et al. | |
| 6,143,354 A | 11/2000 | Koulik et al. | |
| 6,153,252 A | 11/2000 | Hossainy et al. | 427/2.3 |
| 6,159,978 A | 12/2000 | Myers et al. | |
| 6,165,212 A | 12/2000 | Dereume et al. | 62/1.13 |
| 6,172,167 B1 | 1/2001 | Stapert et al. | |
| 6,177,523 B1 | 1/2001 | Reich et al. | |
| 6,180,632 B1 | 1/2001 | Myers et al. | |
| 6,203,551 B1 | 3/2001 | Wu | |
| 6,211,249 B1 | 4/2001 | Cohn et al. | |
| 6,214,901 B1 | 4/2001 | Chudzik et al. | |
| 6,231,600 B1 | 5/2001 | Zhong | |
| 6,240,616 B1 | 6/2001 | Yan | |
| 6,245,753 B1 | 6/2001 | Byun et al. | |
| 6,245,760 B1 | 6/2001 | He et al. | |
| 6,248,129 B1 | 6/2001 | Froix | |
| 6,251,136 B1 | 6/2001 | Guruwaiya et al. | |
| 6,254,632 B1 | 7/2001 | Wu et al. | |
| 6,258,121 B1 | 7/2001 | Yang et al. | |
| 6,258,371 B1 | 7/2001 | Koulik et al. | |
| 6,262,034 B1 | 7/2001 | Mathiowitz et al. | |
| 6,270,788 B1 | 8/2001 | Koulik et al. | |
| 6,277,449 B1 | 8/2001 | Kolluri et al. | |
| 6,283,947 B1 | 9/2001 | Mirzaee | |
| 6,283,949 B1 | 9/2001 | Roorda | |
| 6,284,305 B1 | 9/2001 | Ding et al. | |
| 6,287,628 B1 | 9/2001 | Hossainy et al. | |
| 6,299,604 B1 | 10/2001 | Ragheb et al. | |
| 6,306,176 B1 | 10/2001 | Whitbourne | |
| 6,331,313 B1 | 12/2001 | Wong et al. | |
| 6,335,029 B1 | 1/2002 | Kamath et al. | |
| 6,344,035 B1 | 2/2002 | Chudzik et al. | |
| 6,346,110 B2 | 2/2002 | Wu | |
| 6,358,556 B1 | 3/2002 | Ding et al. | |
| 6,379,381 B1 | 4/2002 | Hossainy et al. | |
| 6,387,379 B1 | 5/2002 | Goldberg et al. | |
| 6,395,326 B1 | 5/2002 | Castro et al. | |
| 6,419,692 B1 | 7/2002 | Yang et al. | |
| 6,451,373 B1 | 9/2002 | Hossainy et al. | |
| 6,482,834 B2 | 11/2002 | Spada et al. | |
| 6,494,862 B1 | 12/2002 | Ray et al. | |
| 6,503,538 B1 | 1/2003 | Chu et al. | |
| 6,503,556 B2 | 1/2003 | Harish et al. | |
| 6,503,954 B1 | 1/2003 | Bhat et al. | |
| 6,506,437 B1 | 1/2003 | Harish et al. | |
| 6,524,347 B1 | 2/2003 | Myers et al. | |
| 6,527,801 B1 | 3/2003 | Dutta | |
| 6,527,863 B1 | 3/2003 | Pacetti et al. | |
| 6,528,526 B1 | 3/2003 | Myers et al. | |
| 6,530,950 B1 | 3/2003 | Alvarado et al. | |
| 6,530,951 B1 | 3/2003 | Bates et al. | |
| 6,540,776 B2 | 4/2003 | Sanders Millare et al. | |
| 6,544,223 B1 | 4/2003 | Kokish | |
| 6,544,543 B1 | 4/2003 | Mandrusov et al. | |
| 6,544,582 B1 | 4/2003 | Yoe | |
| 6,555,157 B1 | 4/2003 | Hossainy | |
| 6,558,733 B1 | 5/2003 | Hossainy et al. | |
| 6,565,659 B1 | 5/2003 | Pacetti et al. | |
| 6,572,644 B1 | 6/2003 | Moein | |
| 6,585,755 B2 | 7/2003 | Jackson et al. | |
| 6,585,765 B1 | 7/2003 | Hossainy et al. | |
| 6,585,926 B1 | 7/2003 | Mirzaee | |
| 6,605,154 B1 | 8/2003 | Villareal | |
| 6,616,765 B1 | 9/2003 | Hossainy et al. | |
| 6,623,448 B2 | 9/2003 | Slater | |
| 6,625,486 B2 | 9/2003 | Lundkvist et al. | |
| 6,645,135 B1 | 11/2003 | Bhat | |
| 6,645,195 B1 | 11/2003 | Bhat et al. | |
| 6,656,216 B1 | 12/2003 | Hossainy et al. | |
| 6,656,506 B1 | 12/2003 | Wu et al. | |
| 6,660,034 B1 | 12/2003 | Mandrusov et al. | |
| 6,663,662 B2 | 12/2003 | Pacetti et al. | |
| 6,663,880 B1 | 12/2003 | Roorda et al. | |
| 6,666,880 B1 | 12/2003 | Chiu et al. | |
| 6,673,154 B1 | 1/2004 | Pacetti et al. | |
| 6,673,385 B1 | 1/2004 | Ding et al. | |
| 6,689,099 B2 | 2/2004 | Mirzaee | |
| 6,695,920 B1 | 2/2004 | Pacetti et al. | |
| 6,706,013 B1 | 3/2004 | Bhat et al. | |
| 6,709,514 B1 | 3/2004 | Hossainy | |
| 6,712,845 B2 | 3/2004 | Hossainy | |
| 6,713,119 B2 | 3/2004 | Hossainy et al. | |
| 6,716,444 B1 | 4/2004 | Castro et al. | |
| 6,723,120 B2 | 4/2004 | Yan | |
| 6,733,768 B2 | 5/2004 | Hossainy et al. | |
| 6,740,040 B1 | 5/2004 | Mandrusov et al. | |

| | | |
|---|---|---|
| 6,743,462 B1 | 6/2004 | Pacetti |
| 6,749,626 B1 | 6/2004 | Bhat et al. |
| 6,753,071 B1 | 6/2004 | Pacetti et al. |
| 6,758,859 B1 | 7/2004 | Dang et al. |
| 6,759,054 B2 | 7/2004 | Chen et al. |
| 6,764,505 B1 | 7/2004 | Hossainy et al. |
| 2001/0007083 A1 | 7/2001 | Roorda |
| 2001/0014717 A1 | 8/2001 | Hossainy et al. |
| 2001/0018469 A1 | 8/2001 | Chen et al. |
| 2001/0020011 A1 | 9/2001 | Mathiowitz et al. |
| 2001/0029351 A1 | 10/2001 | Falotico et al. |
| 2001/0037145 A1 | 11/2001 | Guruwaiya et al. |
| 2001/0051608 A1 | 12/2001 | Mathiowitz et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0009604 A1 | 1/2002 | Zamora et al. |
| 2002/0016625 A1 | 2/2002 | Falotico et al. |
| 2002/0032414 A1 | 3/2002 | Ragheb et al. |
| 2002/0032434 A1 | 3/2002 | Chudzik et al. |
| 2002/0051730 A1 | 5/2002 | Bodnar et al. |
| 2002/0071822 A1 | 6/2002 | Uhrich |
| 2002/0077693 A1 | 6/2002 | Barclay et al. |
| 2002/0082679 A1 | 6/2002 | Sirhan et al. |
| 2002/0087123 A1 | 7/2002 | Hossainy et al. |
| 2002/0091433 A1 | 7/2002 | Ding et al. |
| 2002/0094440 A1 | 7/2002 | Llanos et al. |
| 2002/0111590 A1 | 8/2002 | Davila et al. |
| 2002/0120326 A1 | 8/2002 | Michal |
| 2002/0123801 A1 | 9/2002 | Pacetti et al. |
| 2002/0142039 A1 | 10/2002 | Claude |
| 2002/0155212 A1 | 10/2002 | Hossainy |
| 2002/0165608 A1 | 11/2002 | Llanos et al. |
| 2002/0176849 A1 | 11/2002 | Slepian |
| 2002/0183581 A1 | 12/2002 | Yoe et al. |
| 2002/0188037 A1 | 12/2002 | Chudzik et al. |
| 2002/0188277 A1 | 12/2002 | Roorda et al. |
| 2003/0004141 A1 | 1/2003 | Brown |
| 2003/0028243 A1 | 2/2003 | Bates et al. |
| 2003/0028244 A1 | 2/2003 | Bates et al. |
| 2003/0031780 A1 | 2/2003 | Chudzik et al. |
| 2003/0032767 A1 | 2/2003 | Tada et al. |
| 2003/0036794 A1 | 2/2003 | Ragheb et al. |
| 2003/0039689 A1 | 2/2003 | Chen et al. |
| 2003/0040712 A1 | 2/2003 | Ray et al. |
| 2003/0040790 A1 | 2/2003 | Furst |
| 2003/0059520 A1 | 3/2003 | Chen et al. |
| 2003/0060877 A1 | 3/2003 | Falotico et al. |
| 2003/0065377 A1 | 4/2003 | Davila et al. |
| 2003/0072868 A1 | 4/2003 | Harish et al. |
| 2003/0073961 A1 | 4/2003 | Happ |
| 2003/0083646 A1 | 5/2003 | Sirhan et al. |
| 2003/0083739 A1 | 5/2003 | Cafferata |
| 2003/0087111 A1 * | 5/2003 | Hubbell et al. .............. 428/457 |
| 2003/0097088 A1 | 5/2003 | Pacetti |
| 2003/0097173 A1 | 5/2003 | Dutta |
| 2003/0099712 A1 | 5/2003 | Jayaraman |
| 2003/0105518 A1 | 6/2003 | Dutta |
| 2003/0113439 A1 | 6/2003 | Pacetti et al. |
| 2003/0150380 A1 | 8/2003 | Yoe |
| 2003/0157241 A1 | 8/2003 | Hossainy et al. |
| 2003/0158517 A1 | 8/2003 | Kokish |
| 2003/0190406 A1 | 10/2003 | Hossainy et al. |
| 2003/0207020 A1 | 11/2003 | Villareal |
| 2003/0211230 A1 | 11/2003 | Pacetti et al. |
| 2004/0018296 A1 | 1/2004 | Castro et al. |
| 2004/0029952 A1 | 2/2004 | Chen et al. |
| 2004/0047978 A1 | 3/2004 | Hossainy et al. |
| 2004/0047980 A1 | 3/2004 | Pacetti et al. |
| 2004/0052858 A1 | 3/2004 | Wu et al. |
| 2004/0052859 A1 | 3/2004 | Wu et al. |
| 2004/0054104 A1 | 3/2004 | Pacetti |
| 2004/0060508 A1 | 4/2004 | Pacetti et al. |
| 2004/0062853 A1 | 4/2004 | Pacetti et al. |
| 2004/0063805 A1 | 4/2004 | Pacetti et al. |
| 2004/0071861 A1 | 4/2004 | Mandrusov et al. |
| 2004/0072922 A1 | 4/2004 | Hossainy et al. |
| 2004/0073298 A1 | 4/2004 | Hossainy |
| 2004/0086542 A1 | 5/2004 | Hossainy et al. |
| 2004/0086550 A1 | 5/2004 | Roorda et al. |
| 2004/0096504 A1 | 5/2004 | Michal |
| 2004/0098117 A1 | 5/2004 | Hossainy et al. |

FOREIGN PATENT DOCUMENTS

| | | |
|---|---|---|
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 970 711 A2 * | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| SU | 0 301 856 | 2/1989 |
| SU | 0 396 429 | 11/1990 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18466 | 4/2000 |
| WO | WO 00/64506 | 11/2000 |
| WO | WO 01/01890 A1 * | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/50127 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |

| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 2004/000383 | 12/2003 |
| WO | WO 2004/009145 | 1/2004 |

OTHER PUBLICATIONS

Odian, G. "Steric Effects". Principles of Polymerization. 1991. John Wiley & Sons, Inc. 3rd Ed. p. 695.*

Gauuan et al. "Superoide Dismutase Mimetics: Synthesis and Structure—Activity Relationship Study of MnTBAP Analogues". Bioorganic & Medicinal Chemistry 10 (2002) 3013-3021.*

Wohrle et al. "Polymer-bound porphyrins and their precursors, 10a) Syntheses and photoredox propeties of water-soluble W polymers with covalently bonded zinc tetraphenylporphyrin". Makromol. Chem. 192, 819-832 (1991).*

Anonymous, *Cardiologists Draw—Up The Dream Stent*, Clinica 710:15 (Jun. 17, 1996), http://www.dialogweb.com/cgi/document?req=1061848202959, printed Aug. 25, 2003 (2 pages).

Anonymous, *Heparin-coated stents cut complications by 30%*, Clinica 732:17 (Nov. 18, 1996), http://www.dialogweb.com/cgi/document?req=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?req=1061848017752, printed Aug. 25, 2003 (2 pages).

Aoyagi et al., *Preparation of cross-linked alipathic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Helmus, *Overview of Biomedical Materials*, MRS Bulletin, pp. 33-38, (Sep. 1991).

Herdeg et al., *Antiproliferative Stent Coatings: Taxol and Related Compounds*, Semin. Intervent. Cardiol. 3:197-199 (1998).

Huang et al., *Biodegradable Polymers Derived from Aminoacids*, Macromol. Symp. 144, 7-32 (1999).

Inoue et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Katsarava et al., *Amino Acid-Based Bioanalogous Polymer. Synthesis and Study of Regular Poly(ester amide)s Based on Bis($\alpha$-amino acid)$\alpha$,$\omega$-Alkylene Diesters, and Aliphatic Dicarbolic Acids*, Journal of Polymer Science, Part A: Polymer Chemistry, 37(4), 391-407 (1999).

Levy et al., *Strategies For Treating Arterial Restenosis Using Polymeric Controlled Release Implants*, Biotechnol. Bioact. Polym. [Proc. Am. Chem. Soc. Symp.], pp. 259-2968 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials For Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, EPO Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol)Multiblock Copolymer as a Carrier of Anti-Cancer Drug Doxorubicin*, Bioconjugate Chemistry 11(2):131-139 (Mar./Apr. 2000).

Peng et al., *Role of polymers in improving the results of stenting in coronary arteries*, Biomaterials 17:685-694 (1996).

Saotome, et al., *Novel Enzymatically Degradable Polymers Comprising $\alpha$-Amino Acid, 1,2-Ethanediol, and Adipic Acid*, Chemistry Letters, pp. 21-24 (1991).

Shigeno, *Prevention of Cerebrovascular Spasm By Bosentan, Novel Endothelin Receptor*, Chemical Abstract 125:212307 (1996).

van Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

* cited by examiner

BIOCOMPATIBLE COATING FOR IMPLANTABLE MEDICAL DEVICES

BACKGROUND OF THE INVENTION

1. Field of the Invention

This invention is directed to coatings for implantable medical devices, such as drug eluting vascular stents.

2. Description of the State of the Art

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against the atherosclerotic plaque of the lesion to remodel the lumen wall. The balloon is then deflated to a smaller profile to allow the catheter to be withdrawn from the patient's vasculature. polymer dissolved in the solvent, and a therapeutic substance dispersed in the blend is applied to the stent. The solvent is allowed to evaporate, leaving on the stent surface a coating of the polymer and the therapeutic substance impregnated in the polymer. Once the stent has been implanted at the treatment site, the therapeutic substance has a sustained release profile from the polymer.

Although local administration of therapeutic agents via stents has shown favorable results in reducing restenosis, improvements can be made to the coatings, more particularly improvements of the biological compatibility of the coatings. The embodiments of the present invention provide for biologically compatible polymers and combination of polymers for coating stents and other implantable medical devices.

SUMMARY

A coating for an implantable medical device is provided, the coating includes a copolymer, the copolymer comprising at least one biologically compatible structural moiety and at least one biologically active moiety. The structural moiety can comprise unsubstituted or substituted acrylates, and can be derived from methyl methacrylate, n-butyl methacrylate, lauryl methacrylate, 2-hydroxyethyl methacrylate, or styrene. The biologically active moiety can be derived from superoxide dismutate-mimetics, diazenium diolate type nitric oxide donors, polycationic peptides, polysaccharides, for example, heparin or heparin derivatives, pyrrolidone, poly (ethylene glycol), vitamin E, sulfonated dextran, β-phenoxy-etanol, N,N-dimethylamino-2-ethanol, mannose-6-phosphate, sulfonic acid and derivatives of sulfonic acid such as propanesulfonic acid, 2-methyl-1-propanesulfonic acid, benzenesulfonic acid, and 3-methoxy-2-hydroxypropane-sulfonic acid. The copolymer can be a block copolymer made by living free radical copolymerization of plurality of monomers with initiation, transfer, termination (iniferter) of the living macro-chains.

A method for coating an implantable medical device is disclosed, the method comprising depositing a copolymer comprising at least one biologically compatible structural moiety and at least one biologically active moiety onto the device.

A biologically compatible copolymer is disclosed, the copolymer having a formula

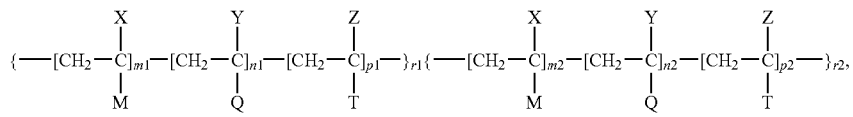

wherein m1, n1, p1, r1, m2, n2, p2, and r2 is each, independently, an integer and m1≧0, n1>0, p1≧0, r1>0, m2≧0, n2>0, p2≧0, r2>0;

with the provision that if m1=0, then p1>0; or if p1=0, then m1>0; or if m2=0, then p2>0; or if p2=0, then m2>0;

X, Y, and Z can be each, independently, hydrogen or an alkyl group; M and T can be each, independently, an ester group or a substituted or unsubstituted aryl group; and Q is a biologically active moiety.

DETAILED DESCRIPTION

A coating for an implantable medical device, such as a stent, according to one embodiment of the present invention, can include an optional primer layer, a drug-polymer layer (also referred to as "reservoir" or "reservoir layer") or alternatively a polymer free drug layer, and an optional topcoat layer. The drug-polymer layer serves as a reservoir for the drug. The reservoir layer or the polymer free drug layer can be applied directly onto the stent surface. The optional primer layer can be applied on the stent surface to improve the adhesion of the drug-polymer layer or the polymer free drug layer to the stent. The optional topcoat layer, which can be essentially free from any drugs, serves as a rate limiting membrane which helps to control the rate of release of the drug.

According to embodiments of the present invention, biologically compatible copolymers can be used to fabricate the reservoir layer and the optional primer and topcoat layers. To fabricate the coating, the copolymer can be dissolved in a suitable solvent and the solution can be applied onto a stent, for example, by spraying. A variety of solvents or blends thereof can used. Those having ordinary skill in the art can select a suitable solvent or a blend of solvents depending on particular copolymer that is used for making the stent coating. The solvent is allowed to evaporate leaving a coating adhered to the stent. To accelerate the removal of the solvent, the coated stent can be baked.

The biologically compatible copolymers can be either random copolymers or block copolymers. The term "random copolymer" is defined in accordance with terminology used by the International Union of Pure and Applied Chemistry (IUPAC). The IUPAC defines a random copolymer as a copolymer consisting of macromolecules in which the probability of finding a given monomeric unit at any given site in the chain is independent of the nature of the adjacent units. In a random copolymer, the sequence distribution of monomeric units follows Bernoullian statistics.

The term "block copolymer" used in the present invention is defined as a copolymer containing a linear arrangement of blocks, a block being defined as a portion of a polymer molecule in which the monomeric units have at least one constitutional or configurational feature absent from the adjacent portions. For example, a block copolymer of moiety A and moiety B may be written as -A-A-A-B-B-B-B-. Such block copolymer is often referred to as a "AB block copolymer." The blocks need not be linked on the ends, since the individual blocks are usually long enough to be considered polymers in their own right. The AB block copolymer can be, accordingly, named poly A-block-poly B.

The term "block copolymer" is intended to broadly include two or more types of blocks such as tri-blocks, tetra-blocks, and so on. In addition to AB block copolymers, variations of other available block copolymers include ABA block copolymers (-A-A-A-B-B-B-A-A-A-), ABCBA block copolymers (-A-A-A-B-B-B-C-C-C-B-B-B-A-A-A-), ABC block copolymers (-A-A-A-B-B-B-C-C-C-), etc.

Either random copolymers or block copolymers that can be used to fabricate a coating or a layer of a stent coating can include at least one biologically compatible structural moiety and at least one biologically active moiety. For example, in case of random copolymers, some constituent units of the copolymers can include the biologically compatible moiety while other constituent units can include the biologically active moiety. In case of AB block copolymers, either moiety A or moiety B can be a structural moiety, and the other moiety can be a biologically active moiety. As another example, for an ABC block copolymer, either moiety A, B, or C, or any two of A, B, and C can be a structural moiety or moieties, while the remaining moiety or moieties can be a biologically active moiety or moieties.

In general, one example of a structure of block copolymers that can be used can be illustrated by formula (I):

unsubstituted aryl group, where the substitutents in the aryl group include halogens, hydroxyl, carboxyl or amino groups; and (e) Q is a chemical fragment providing the B-units with biologically active properties, which can be attached to the backbone of the block copolymer in a variety of ways, for example via the acyl group or via the methylene bridge.

The structure of a random copolymer is generally similar to the structure of formula (I), except the A-, B-, and C-units in the random copolymer are distributed randomly and not in blocks.

Examples of biologically active fragments that can be incorporated into the random or block copolymer include the fragments derived from superoxide dismutate-mimetics ($SOD_m$), diazenium diolate type nitric oxide donors, polycationic peptides, polysaccharides, for example, heparin or heparin derivatives, pyrrolidone, poly(ethylene glycol) (PEG), vitamin E, sulfonated dextrane, β-phenoxyetanol, N,N-dimethylamino-2-ethanol, mannose-6-phosphate, sulfonic acid and derivatives of sulfonic acid such as propanesulfonic acid, 2-methyl-1-propanesulfonic acid, benzenesulfonic acid, and 3-methoxy-2-hydroxypropanesulfonic acid.

Superoxide dismutate-mimetics are oxidoreductases-based complexes that contain cations of copper, iron, or manganese. SOD-mimetics are major intracellular enzymes that protect the cell against oxygen toxicity by dismutating the radical oxygen superoxide, $O_2^-$, to oxygen and hydrogen peroxide. A complex seven-ligand manganese-based $SOD_m$, manganese(II)dichloro-aminoethylthiolated pentaazatetracyclohexacosatriene (SOD-40470) manufactured by Metaphore Pharmaceuticals, Inc., St. Louis, Mo. is one example of $SOD_m$ that can be used in preparing the B-units of the block copolymer of formula (I). Other types of $SOD_m$ can be also used, if desired.

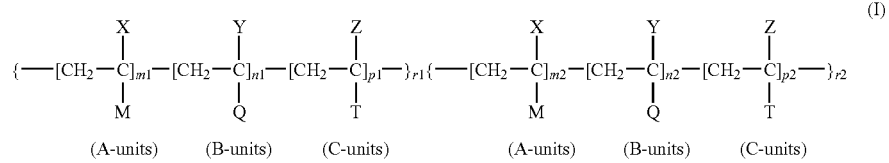

(A-units)  (B-units)  (C-units)  (A-units)  (B-units)  (C-units)

wherein:

(a) m1, n1, p1, r1, m2, n2, p2, and r2 are all integers, wherein m1≧0, n1>0, p1≧0, r1>0, m2≧0, n2>0, p2≧0, r2>0;

if m1=0, then p1>0, and if p1=0, then m1>0; and m2=0, then p2>0, and if p2=0, then m2>0;

each member r1 and r2, etc. of the sequence r1, r2 . . . can be the same or different; m1 and m2 can be the same or different; n1 and n2 can be the same or different; and p1 and p2 can be the same or different;

(b) X, Y, and Z is each, independently, hydrogen or an alkyl group, for example, methyl group, and X, Y, and Z can be the same or different;

(c) M and T is each, independently, an ester group —C(O)—OR, or a substituted or unsubstituted aryl group, where the substitutents in the aryl group include halogens, hydroxyl, carboxyl or amino groups, and M and T can be the same or different;

(d) R in the ester group is a straight-chained or branched substituted or unsubstituted alkyl group, or substituted or Diazenium diolate type nitric oxide donors are adducts of nitric oxide (NO) with nucleophilic amines. Diazenium diolates, also known as NONOates, are highly biologically compatible and possess valuable medicinal properties. In slightly acidic medium they spontaneously release NO which has excellent therapeutical properties. One example of diazenium diolate that can be used for making the B-units of block copolymers of formula (I) is an aliphatic NONOate 1,3-propanediamine, N-{4-[1-(3-aminopropyl)-2-hydroxy-2-nitrosohydrazino] butyl}-diazen-1 -ium-1,2-diolate also known as spermine diazenium diolate (SDD) and having the formula $NH_2$—$(CH_2)_3$—$N[N^+(O)$—$(N$—$OH)]$—$(CH_2)_4$—$NH$—$(CH_2)_3$—$NH_2$. SDD is manufactured by Molecular Probes, Inc., Eugene, Oreg. Alternatively, other diazenium diolate-type NO donors can be used. One example of a suitable alternative diazenium diolate-type NO donor can be 1-{N-methyl-N-[6-(N-methylammonio)hexyl] amino}diazen-1-ium-1,2-diolate having the formula $CH_3$—$N^+H_2$—$(CH_2)_6$—$N(CH_3)$—$N^+(O^-)$=$N$—$O^-$ (MAHMA-NO). Another example of a suitable alternative NONOate can be and Z-1-[N-(2-aminoethyl)-N-(2-ammonioethyl)amino]

diazen-1-ium-1,2-diolate having the formula O⁻—N⁺[N(CH₂—CH₂—NH₂)CH₂—CH₂—N⁺H₃]=N—O⁻ (DETA-NO). MAHMA-NO and DETA-NO can be obtained from Cayman Chemical Co., Ann Arbor, Mich.

Examples of suitable polycationic peptides that can be used to make the B-units of the block copolymer of formula (I) include poly(L-arginine), poly(D-arginine), poly(D,L-arginine), poly(L-lysine), poly(D-lysine), poly(δ-guanido-α-aminobutyric acid), and a racemic mixture of poly(L-arginine) or poly(D-arginine). The terms "poly(L-arginine)," "poly(D-arginine)," "poly(D,L-arginine)" are intended to include L-, D-, and/or D,L-arginine in both its polymeric and oligomeric form. Arginine (R or 2-amino-5-guanidinovaleric acid), is an amino acid having a formula

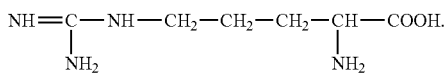

Polymers and/or oligomers of L-, D-, and/or D, L-arginine that can be used comprise a plurality of repeating monomeric amino acid units connected with peptide bonds, each unit including 1-guanidinopropyl radical having the structure —CH₂—CH₂—CH₂—NH—C(NH₂)=NH. For example, a heptamer (R7) (p=7), or a nonamer (R9) (p=9) of L-arginine, can be used.

Heparin is derived from a mixture of sulfated polysaccharide chains based on D-glucosamine and D-glucuronic or L-iduronic acid. "Heparin derivative" is intended to include any functional or structural variation of heparin. Representative variations include heparinoids, heparin having a hydrophobic counter-ion, heparan sulfate, alkali metal or alkaline-earth metal salts of heparin, for example, sodium heparin (also known as hepsal or pularin), potassium heparin (formerly known as clarin), lithium heparin, calcium heparin (also known as calciparine), magnesium heparin (also known as cutheparine), low molecular weight heparin (also known as ardeparin sodium), and blends thereof. Examples of other suitable polysaccharides that can be included in the B-units of the block copolymer of formula (I) are glycosaminoglycans (or mucopolysaccharides) such as keratan sulfate, chondroitin sulfate, dermatan sulfate (also known as chondroitin sulfate B), hyaluronic acid, hyaluronates and blends thereof.

As seen from formula (I), the block copolymer can have three types of units A, B, and C to include block copolymers such as ABC or ABCBA block copolymers (if M and T are different), or two types of units A and B to include block copolymers such as AB or ABA. A-units or C-units or both A- and C-units are the structural moiety or moieties, and B-units are the biologically active moiety.

Block copolymers of formula (I) are expected to evince not only good biocompatibility (e.g., blood compatibility) but also good physical, chemical and mechanical properties suitable for making medicated stent coatings. In addition, due to the presence of the biologically active moiety, the block copolymers are expected to elicit favorable biological effects such as, for example, preventing significant platelet aggregation or inflammation, being non-supportive to smooth muscular cells on the surface, and causing endothelialization (self-healing) on the surface. The block copolymers used in the coatings of the present invention can also have a potential for synergistic biological effect when used together with at least some drugs used in the reservoir layer or the drug layer of the coating.

The random or block copolymers represented by formula (I) can be obtained by common synthetic methods, for example, by radical copolymerization of monomers forming A-, B-, and/or C-units in bulk, solution, suspension, or emulsion, in the presence of suitable initiators. For preparing the block copolymers, one synthetic method that can be used is the method of living free radical copolymerization with initiation, transfer, termination (iniferter) of the living macrochains (the iniferter process). The iniferter process utilizes an initiator capable of undergoing thermal and/or photolytic free radical decomposition. Examples of suitable initiators include benzyl-N,N-diethyldithiocarbamate (BDC) or p-xylylene-N,N-diethyldithiocarbamate (XDC). BDC is a derivative of toluene and has the formula C₆H₅—CH₂—S—C(S)—N—(C₂H₅)₂. XDC is a derivative of p-xylene and has the formula (C₂H₅)₂—N—C(S)—S—CH₂—C₆H₄—CH₂—S—C(S)—N—(C₂H₅)₂. One possible path of the process of decomposition of an initiator is shown for BDC by scheme (II):

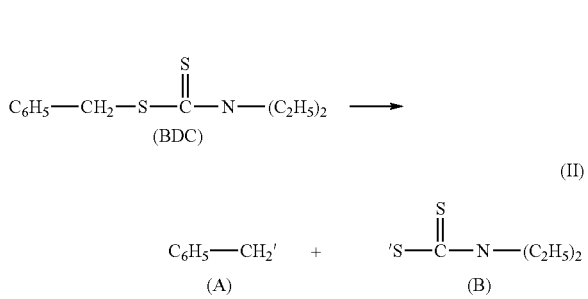

As a result of decomposition of BDC, two types of radicals are generated: the benzylic radical (species A), which undergoes free-radical addition to a monomer molecule initiating polymerization, and the dithiocarbamate radical which terminates by heterolytic radical combination. One possible path of polymerization is shown by reaction schemes (III) and (IV):

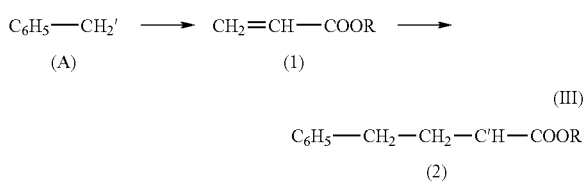

In reaction (III), radical A serves as a free-radical initiator reacting with the monomer 1 creating reactive species (2), which can further react with radical B acting as a transfer agent terminator. The reactive species (3) shown by reaction (IV) below, in the presence of monomer and light will undergo heterolytic cleavage yielding the reactive polymer chain and the chain transfer agent, species B. The process is propagated until monomer (1) has been consumed:

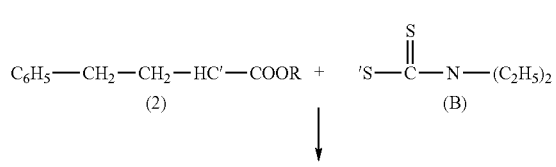

-continued

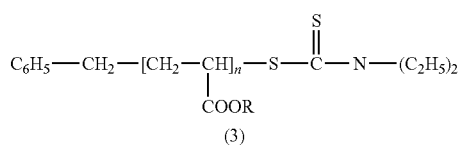

Following the completion of polymerization, another monomer can be added and the process analogous to the process described by reactions (II)-(IV) can be repeated, resulting in formation of an AB block copolymer. If a difunctional or multifunctional inferter is used, an ABA, ABCBA, etc., block or star-block copolymers can be obtained in a similar fashion.

1. Monomers Forming the Structural Moiety

The structural moiety forming the random or block copolymer (A- and/or C-units in formula I) can be derived from unsaturated monomers, for example, unsubstituted or substituted acrylates or a general formula $CH_2=CX-M$, where X is hydrogen or methyl and M is a substituted or unsubstituted aryl group or an ester group $O=C(OR)-$, where R is an alkyl or aryl.

Some monomers that can be used to form the structural moiety are summarized in Table 1. Other monomers described by the formula $CH_2=CX-M$ can be used, if desired.

Examples of the monomers and/or oligomers from which anti-restenotic moiety can be derived include acryloyl-, methacryloyl-, vinyl or allyl-modified adducts of $SOD_m$, acryloyl-, methacryloyl-, vinyl or allyl-modified donors of NO (examples of the NO donors include DETA or speramine), and acryloyl-, methacryloyl-, vinyl or allyl-modified polycationic peptides such as poly-L-arginine.

Examples of some particular monomers that can be used to form the biologically active moiety include 2-acrylamido-2-methyl-1-propanesulfonic acid, poly(ethylene glycol) methacrylate, 3-sulfopropyl acrylate, 3-sulfopropyl methacrylate, N-vinylpyrrolidone, vinylsulfonic acid, 4-styrenesulfonic acid and 3-allyloxy-2-hydroxypropanesulfonic acid. All monomers based on sulfonic acid can be either in a form of an acid or in a form of an alkali metal salt (e.g., $K^+$ or $Na^+$).

3. Initiators

For synthesis of random block copolymers, standard initiators of radical homo- or copolymerization can be used, for example, 2,2-dimethoxy-2-phenol acetophenone. Benzophenone can be optionally added to 2,2-dimethoxy-2-phenol acetophenone as a photosensitizer.

Examples of suitable initiators for synthesis of block copolymers include BDC or XDC described above. The initiators can be prepared synthetically. To synthesize BDC, sodium N,N-diethyldithiocarbamate can be combined with benzyl bromide in an anhydrous methanol solution. The ratio between sodium N,N-diethyldithiocarbamate and benzyl bromide can be close to equimolar. The mixture can be stirred for about 24 hours at about room temperature to yield BDC.

TABLE 1

Examples of monomers $CH_2=CX-M$ that can be used to form the structural moiety of the random or block copolymer.

| No. | Monomer | Abbreviation | X | M |
|---|---|---|---|---|
| 1 | Methyl methacrylate | MMA | $CH_3$ | $-C(=O)-OCH_3$ |
| 2 | Ethyl methacrylate | EMA | $CH_3$ | $-C(=O)-O-CH_2-CH_3$ |
| 3 | n-Butyl methacrylate | BMA | $CH_3$ | $-C(=O)-O-CH_2-CH_2-CH_2-CH_3$ |
| 4 | Lauryl methacrylate | LMA | $CH_3$ | $-C(=O)-O-(CH_2)_{11}-CH_3$ |
| 5 | 2-Hydroxyethyl methacrylate | HEMA | $CH_3$ | $-C(=O)-O-CH_2-CH_2-OH$ |
| 6 | Styrene (vinyl benzene) | ST | H | $-C_6H_5$ |

2. Monomers Forming the Biologically Active Moiety

The biologically active moiety forming the random or block copolymer (B-units in formula I) can be derived from unsaturated monomers and/or oligomers. The choice of the monomer and/or oligomer depends on the kind of biological response that the biologically active moiety is designed to elicit. For example, the biologically active moiety can provide anti-restenotic effect (to treat restenosis), or to ensure better blood compatibility, or to promote cell adhesion.

The process can be completed by evaporating methanol at a reduced pressure and vacuum distillation. The synthesis of XDC is similar, except instead of benzyl bromide, α,α-dibromo-p-xylene is used, and the molar ratio between sodium N,N-diethyldithiocarbamate and α,α-dibromo-p-xylene can be about 1:2.3. The product of reaction is XDC which can be purified by re-crystallization in methanol.

The coating can be used as a reservoir layer containing an active agent or a drug, or a topcoat layer for reducing the rate of release of the drug. The block copolymers can be used alone or in combination with other suitable polymers. In other words, the copolymer can be blended or layered with other polymers Poly(ethylene-co-vinyl alcohol) (EVAL) is one example of a polymer than can be employed. EVAL is a product of hydrolysis of ethylene-vinyl acetate copolymers and may also be a terpolymer including up to 5 molar % of units derived from styrene, propylene and other suitable unsaturated monomers.

Representative examples of other suitable polymers include poly(hydroxyvalerate), poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), poly(glycerol-sebacate), polyphosphoester, polyphosphoester urethane; poly(amino acids), cyanoacrylates, poly (trimethylene carbonate), poly(iminocarbonate), co-poly (ether-esters) (e.g. PEO/PLA), polyalkylene oxalates, polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers, vinyl halide polymers and copolymers (such as polyvinyl chloride), polyvinyl ethers (such as polyvinyl methyl ether), polyvinylidene halides (such as polyvinylidene fluoride and polyvinylidene chloride), polyacrylonitrile, polyvinyl ketones, polyvinyl aromatics (such as polystyrene), polyvinyl esters (such as polyvinyl acetate), copolymers of vinyl monomers with each other and olefins (such as ethylene-methyl methacrylate copolymers, acrylonitrile-styrene copolymers, ABS resins, and ethylene-vinyl acetate copolymers), polyamides (such as Nylon 66 and polycaprolactam), alkyd resins, other polycarbonates, polyoxymethylenes, polyimides, polyethers, epoxy resins, other polyurethanes, rayon, rayon-triacetate, cellulose, cellulose acetate, cellulose butyrate, cellulose acetate butyrate, cellophane, cellulose nitrate, cellulose propionate, cellulose ethers, soluble fluorinated polymers and carboxymethyl cellulose.

The embodiments of the present invention are described in connection with a stent, e.g., balloon expandable or self-expandable stents; however, other implantable medical devices can also be coated with the described block copolymers. Examples of such implantable devices include stent-grafts, grafts (e.g., aortic grafts), artificial heart valves, cerebrospinal fluid shunts, pacemaker electrodes, and endocardial leads (e.g., FINELINE and ENDOTAK, available from Guidant Corp. of Santa Clara, Calif.). The underlying structure of the device can be of virtually any design. The device can be made of a metallic material or an alloy such as, but not limited to, cobalt chromium alloy (ELGILOY), stainless steel (316L), "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention.

For the reservoir layer, the coating can include an active agent or a drug. The drug can include any substance capable of exerting a therapeutic or prophylactic effect for a patient. The drug may include small molecule drugs, peptides, proteins, oligonucleotides, and the like. The drug could be designed, for example, to inhibit the activity of vascular smooth muscle cells. It can be directed at inhibiting abnormal or inappropriate migration and/or proliferation of smooth muscle cells to inhibit restenosis.

Examples of drugs include antiproliferative substances such as actinomycin D, or derivatives and analogs thereof (manufactured by Sigma-Aldrich of Milwaukee, Wis., or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S. A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and donors of nitric oxide. An example of an antiallergic agent is permirolast potassium. Other therapeutic substances or agents which may be appropriate include alpha-interferon, genetically engineered epithelial cells, tacrolimus, dexamethasone, and rapamycin and structural derivatives or functional analogs thereof, such as 40-O-(2-hydroxy)ethyl-rapamycin (known by the trade name of EVEROLIMUS available from Novartis), 40-O-(3-hydroxy)propyl-rapamycin, 40-O-[2-(2-hydroxy)ethoxy]ethyl-rapamycin, and 40-O-tetrazole-rapamycin.

Embodiments of the present invention are further illustrated by the following examples Example 1

Synthesis of an ABA Block Copolymer #1

As a first step, a monomer BMA was dissolved in 2-butanone (also known as methyl ethyl ketone) and an initiator XDC was added. The amounts of components are summarized in Table 2.

TABLE 2

Amounts of Components for Synthesis of an ABA Block Copolymer #1 - Step 1

| No. | Component | Experimental amount of the component | |
|---|---|---|---|
| | | mmol | g |
| 1 | BMA | 140.700 | 19.98 |
| 2 | 2-butanone | — | 59.41 |
| 3 | XDC | 0.287 | 0.1151 |

The solution of BMA and XDC in 2-butanone was placed into a borosilicate vial, purged with dry nitrogen for about 30 minutes and the vial was sealed. The contents of vial were subjected to UV radiation at a wavelength within a range of between about 310 nm and about 400 nm, for about 12 hours. The vial was then opened and the contents were added dropwise to ethanol cooled to a temperature of about −76° C. As a result, poly(butylmethacrylate)-XDC (PBMA-XDC) was precipitated. The precipitate was collected using a vacuum funnel and vacuum-dried.

As a second step, PBMA-XDC obtained as described above was combined with 3-sulfopropylmethacrylate and aqueous 2-butanone in the amounts shown in Table 3.

TABLE 3

Amounts of Components for Synthesis of an ABA Block Copolymer #1 - Step 2

| No. | Component | Weight fraction | Amount, grams |
|---|---|---|---|
| 1 | PBMA-XDC | 0.75 | 10.00 |
| 2 | 3-sulfopropylmethacrylate | 0.25 | 3.33 |
| 3 | 2-butanone/water | — | 40.00 |

The blend of PBMA-XDC, 3-sulfopropylmethacrylate, and 2-butanone was placed into a borosilicate vial, purged with dry nitrogen for about 10 minutes and the vial was sealed. The contents of vial were subjected to UV radiation at a wavelength within a range of between about 310 nm and about 400 nm, for about 12 hours. The vial was then opened and the contents were added dropwise to water and vigorously stirred causing precipitation of a poly(3-sulfopropyl methacrylate-block-butylmethacrylate-block-3-sulfopropyhnethacrylate)-XDC. The precipitate was collected using a vacuum funnel and vacuum-dried followed by hydrolysis in the presence of potassium ethoxide to remove the N,N-diethyl-dithiocarbamate functionality. As a result of the described process, poly(3-sulfopropylmethacrylate-block-butylmethacrylate-block-3-sulfopropyl methacrylate), which is an ABA block copolymer, was precipitated, the ABA block copolymer (V):

The, molecular weight of the BMA-based mid-blocks (B blocks) was about 66,700 Daltons as measured by the method of gel-permeation chromatography (GPC) corresponding to the value of n~470, and the molecular weight of the 3-sulfopropylmethacrylate-based end blocks (A blocks) was about 11,100 Daltons, corresponding to values of m~54 and p~54.

Example 2

Synthesis of an ABA Block Copolymer #2

As a first step, PBMA-XDC was synthesized as described in Example 1. As a second step, PBMA-XDC was combined with methacrylic acid (MAA) and 2-butanone in the amounts shown in Table 4.

TABLE 4

Amounts of Components for Synthesis of an ABA Block Copolymer #2 - Step 2

| No. | Component | Theoretical amount of the component | | Experimental amount of the component | |
|---|---|---|---|---|---|
| | | mmol | g | mmol | g |
| 1 | PBMA-XDC | 0.016 | 2.50 | 0.013 | 2.03 |
| 2 | 2-butanone | — | 12.40 | — | 10.19 |
| 3 | Methacrylic acid | 7.20 | 0.625 | 9.10 | 0.78425 |

The blend of PBMA-XDC, methacrylic acid and 2-butanone was subjected to UV radiation at a wavelength within a range of between about 310 nm and about 400 nm, for about 32.5 hours. The vial was then opened, the solvent was removed by evaporation, the contents were dissolved in tetrahydrofuran and the solution was added dropwise to water and vigorously stirred causing precipitation of a poly(methacrylic acid-block-butylmethacrylate-block-methacrylic acid)-XDC. The precipitate was collected using a vacuum funnel and vacuum-dried followed by hydrolysis in the presence of a strong base to remove XDC. As a result of the described process, poly(methacrylic acid-block-butylmethacrylate-block-methacrylic acid), which is an ABA block copolymer, was precipitated, the ABA block copolymer having the general formula (VI):

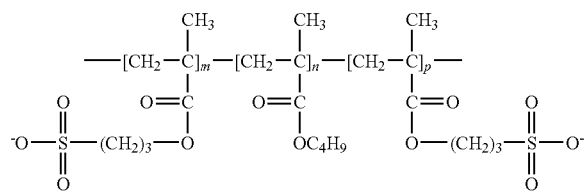

(V)

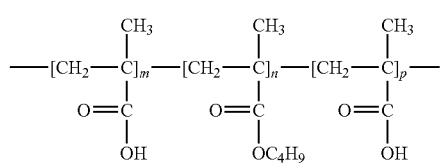

(VI)

The molecular weight of the BMA-based mid-blocks (B blocks) in block-copolymer (VI) was about 85,000 Daltons as measured by GPC corresponding to the value of n~599, and the molecular weight of the methacrylic acid-based end blocks (A blocks) was about 10,020 Daltons, corresponding to values of m~116 and p~116, resulting in molar ratio between units derived from MAA and BMA of about 14:72:14.

Example 3

Synthesis of an ABA Block Copolymer #3

As a first step, PBMA-XDC was synthesized as described in Example 1. As a second step, PBMA-XDC was combined with acryloyl poly(ethylene glycol) (acryloyl-PEG) and 2-butanone in the amounts shown in Table 5.

TABLE 5

Amounts of Components for Synthesis of an ABA Block Copolymer #3 - Step 2

| No. | Component | Theoretical amount of the component | | Experimental amount of the component | |
|---|---|---|---|---|---|
| | | mmol | g | mmol | g |
| 1 | PBMA-XDC | 0.0064 | 1.00 | 0.0059 | 0.93 |
| 2 | 2-butanone | — | 12.40 | — | 10.08 |
| 3 | Acryloyl-PEG | 0.625 | 0.25 | 0.778 | 0.29176 |

Acryloyl-PEG is a product of esterification of acrylic acid by PEG and has a formula (VII):

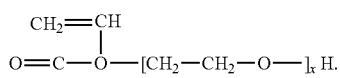

(VII)

A low molecular weight acryloyl-PEG oligomer with the number-averaged molecular weight ($M_n$) of about 375 was used, corresponding to the value "x" in formula of (VII) of about 7. The blend of PBMA-XDC, acryloyl-PEG and 2-butanone was subjected to UV radiation as described in Example 2, for about 43 hours. The vial was then opened, the contents were added dropwise to water and vigorously stirred at a temperature of about 70° C. for about 2 hours, causing evaporation of 2-butanone and forming a suspension of poly(acryloyl-PEG-block-butylmethacrylate-block-acryloyl-PEG)-XDC. The suspension was cooled to the room temperature and the precipitate was collected using a vacuum funnel and vacuum-dried followed by hydrolysis in the presence of a strong base to remove XDC. As a result of the described process, poly(acryloyl-PEG-block-butylmethacrylate-block-acryloyl-PEG), which is a ABA block copolymer, was precipitated, the ABA block copolymer having the general formula (VIII):

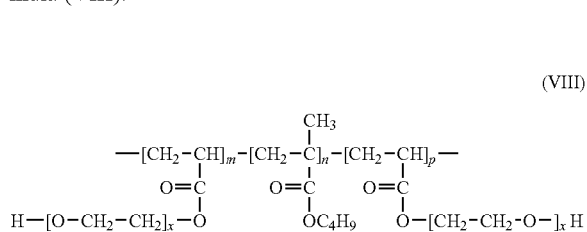

Example 4

Synthesis of an ABCBA Block Copolymer

Poly(3-sulfopropylmethacrylate-block-butylmethacrylate-block-3-sulfopropylmethacrylate)-XDC obtained as described in Example 1 was combined in a borosilicate vial with PEG-methacrylate and 2-butanone in the amounts shown in Table 6.

TABLE 6

Amounts of Components for Synthesis of an ABCBA Block Copolymer

| No. | Component | Weight fraction | Amount, grams |
|---|---|---|---|
| 1 | poly(3-sulfopropylmethacrylate-block-butylmethacrylate-block-3-sulfopropylmethacrylate)-XDC | 0.90 | 10.00 |
| 2 | PEG-methacrylate | 0.10 | 1.10 |
| 3 | 2-butanone | N/A | 33.33 |

A low molecular weight acryloyl-PEG oligomer with $M_n$ of about 375 was used, corresponding to the value "x" in formula of (VII) of about 7'. The mixture in the vial was purged with dry nitrogen for about 10 minutes and the vial was sealed. The contents of vial were subjected to UV radiation at a wavelength within a range of between about 310 nm and about 400 nm, for about 12 hours. The vial was then opened and the contents were added dropwise to water and vigorously stirred causing precipitation of a polymeric matter.

The precipitate was collected using a vacuum funnel and vacuum-dried followed by hydrolysis in the presence of a strong base to remove XDC. As a result of the described process, poly(acryloyl {poly[ethylene glycol]}-block-3-sulfopropylmethacrylate-block-butylmethacrylate-block-3-sulfopropylmethacrylate-block-acryloyl{poly[ethylene glycol]}), which is an ABCBA block copolymer, was precipitated, the ABCBA block copolymer having the general formula (IX):

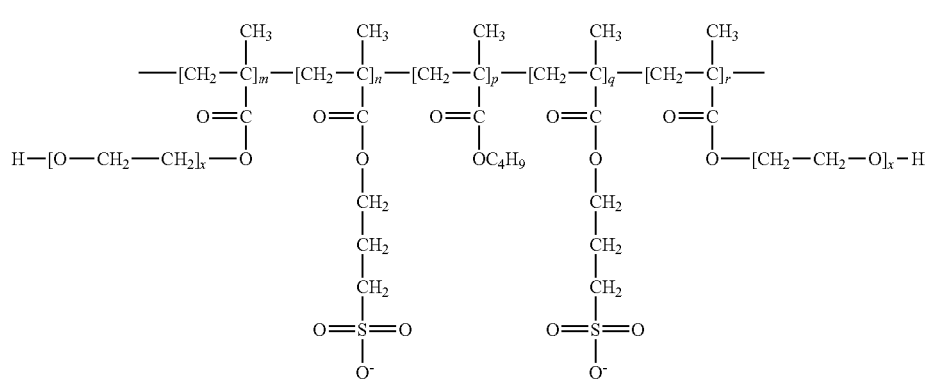

(IX)

The molecular weight of the BMA-based center blocks (C blocks) was about 66,700 Daltons as measured by GPC corresponding to the value of p~470, the molecular weight of the 3-sulfopropylmethacrylate-based blocks (B blocks) was about 11,100 Daltons, corresponding to values of n~54 and q~54, and the molecular weight of terminal PEG-containing blocks (A blocks) was about 4,400 Daltons, corresponding to values of m~12 and r~12.

Example 5

Synthesis of an AB Block Copolymer

As a first step, a monomer BMA was dissolved in 2-butanone and an initiator BDC was added. The amounts of components are summarized in Table 7.

TABLE 7

Amounts of Components for Synthesis
of an AB Block Copolymer - Step 1

| No. | Component | Amount of the component | |
|---|---|---|---|
| | | mmol | g |
| 1 | BMA | 140.8 | 20.0 |
| 2 | 2-butanone | — | 60.0 |
| 3 | BDC | 0.1 | 0.0239 |

The solution of BMA and BDC in 2-butanone was placed into a borosilicate vial, purged with dry nitrogen for about 30 minutes and the vial was sealed. The contents of vial were subjected to UV radiation at a wavelength within a range of between about 310 nm and about 400 nm, for about 12 hours. The vial was then opened and the contents were added dropwise to ethanol cooled to a temperature of about −76° C. As a result, poly(butylmethacrylate)-BDC (PBMA-BDC) was precipitated. The molecular weight of the PBMA-BDC was about 200,000 Daltons as measured by GPC. The precipitate was collected using a vacuum funnel and vacuum-dried.

As a second step, PBMA-BDC obtained as described above was combined with 3-sulfopropylmethacrylate and a 2% (mass) solution of PEG having weight average molecular weight of about 750 in aqueous 2-butanone. The amounts of components are shown in Table 8

TABLE 8

Amounts of Components for Synthesis
of an AB Block Copolymer - Step 2

| No. | Component | Weight fraction | Amount, grams |
|---|---|---|---|
| 1 | PBMA-BDC | 0.75 | 15.00 |
| 2 | 3-sulfopropylmethacrylate | 0.25 | 5.00 |
| 3 | 2% PEG in 2-butanone/water | — | 60.00 |

The blend of PBMA-BDC, 3-sulfopropylmethacrylate, and the PEG solution in aqueous 2-butanone was placed into a borosilicate vial, purged with dry nitrogen for about 10 minutes and the vial was sealed. The contents of vial were subjected to UV radiation at a wavelength within a range of between about 310 nm and about 400 nm, for about 12 hours. The vial was then opened and the contents were added dropwise to water and vigorously stirred causing precipitation of a poly(3-sulfopropylmethacrylate-block-butylmethacrylate)-BDC, having molecular weight of about 266,700 Daltons. The precipitate was collected using a vacuum funnel and vacuum-dried followed by hydrolysis in the presence of a strong base to remove BDC. As a result of the described process, poly(3-sulfopropylmethacrylate-block-butylmethacrylate), which is an AB block copolymer, was precipitated, the AB block copolymer having the general formula (X):

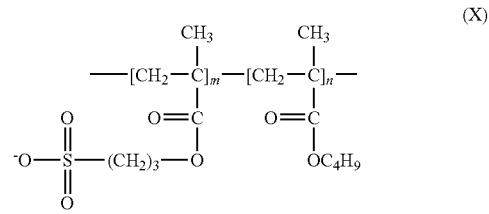

(X)

The molecular weight of the BMA-based blocks (B blocks) was about 200,000 Daltons as measured by GPC corresponding to the value of n~1,400, the molecular weight of the 3-sulfopropylmethacrylate-based blocks (A blocks) was about 66,700 Daltons, corresponding to values of m~324. Overall molecular weight of the block copolymer was about 266,700 Daltons.

Example 6

Synthesis of an ABC Block Copolymer

Poly(3-sulfopropylmethacrylate-block-butylmethacrylate)-BDC obtained as described in Example 5 was combined in a borosilicate vial with PEG-methacrylate and 2-butanone in the amounts shown in Table 9.

TABLE 9

Amounts of Components for Synthesis of an ABC Block Copolymer

| No. | Component | Weight fraction | Amount, grams |
|---|---|---|---|
| 1 | poly(3-sulfopropylmethacrylate-block-butylmethacrylate)-BDC | 0.90 | 15.00 |
| 2 | PEG-methacrylate | 0.10 | 1.66 |
| 3 | 2-butanone | — | 50.00 |

PEG-methacrylate is a product of esterification of methacrylic acid by PEG and has a formula (XI):

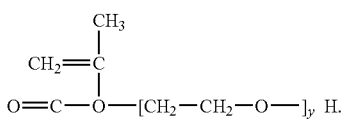

A brand of PEG-methacrylate with the number-averaged molecular weight ($M_n$) of about 520 was used, corresponding to the value "y" in formula of (XI) of about 10. The mixture in the vial was purged with dry nitrogen for about 10 minutes and the vial was sealed. The contents of vial were subjected to UV radiation for about 12 hours. The vial was then opened and the contents were added dropwise to water and vigorously stirred causing precipitation of a polymeric matter. The precipitate was collected using a vacuum funnel and vacuum-dried followed by hydrolysis in the presence of a strong base to remove BDC. As a result of the described process, poly(acryloyl{poly[ethylene glycol]}-block-3-sulfopropyl methacrylate-block-butylmethacrylate), which is a ABC block copolymer (XII) was precipitated:

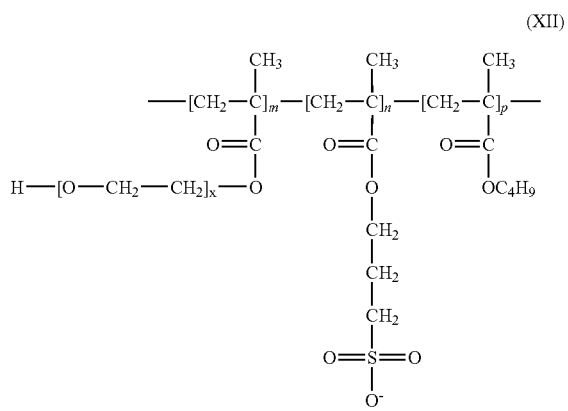

The molecular weight of the BMA-based blocks (C blocks) was about 200,000 Daltons as measured by GPC corresponding to the value of p~1,400, the molecular weight of the 3-sulfopropylmethacrylate-based mid-blocks (B blocks) was about 66,700 Daltons, corresponding to value of n~324, and the molecular weight of the PEG-methacrylate blocks (A blocks) was about 29,600 Daltons, corresponding to value of m~57. Overall molecular weight of the block copolymer was about 296,300 Daltons.

Example 7

Synthesis of a Random Copolymer

A solution can be prepared by thoroughly mixing the following components:
(a) about 15 mass % of MMA;
(b) about 9 mass % of BMA;
(c) about 8 mass % of PEG-methacrylate (PEGMA), where PEG can have weight-average molecular weight of about 6,000;
(d) about 20 mass % of acrylic acid (AA);
(e) about 3 mass % of initiator 2,2-dimethoxy-2-phenol acetophenone; and
(f) the balance of benzene serving as a solvent.

An inert atmosphere can be created by bubbling nitrogen gas through the solution for about 30 minutes. The solution can then be exposed to UV radiation for about 10 minutes at a wavelength of 360 nm while being continuously stirred causing formation of a random copolymer, P(MMA-BMA-AA-PEGMA).

$SOD_m$ can then be grafted to the P(MMA-BMA-AA-PEGMA) copolymer. About 1:1 mole ratio between $SOD_m$ and the amount of acrylic acid can be used. Grafting of $SOD_m$ to the P(MMA-BMA-AA-PEGMA) copolymer can be conducted in the presence of 1-ethyl-3(3-dimethylaminopropyl) carbodiimide, also known as carbodiimide or EDC, having the formula $CH_3—CH_2—N=C=N—CH_2—CH_2—CH_2—N(CH_3)_2$. EDC is manufactured by Pierce Corp., of Rockford, Ill. Instead of EDC, 1,3-dicyclohexylcarbodiimide (DCC) can be used.

The final P(MMA-BMA-AA-PEGMA)-$SOD_m$ random copolymer can be precipitated with a non-solvent such as hexane and vacuum dried. The copolymer can then be mixed with EVAL in a mass ratio of about 2:3 and the mixture can be applied onto a stent to form a reservoir layer or a topcoat layer.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A coating for an implantable medical device, the coating including a block copolymer, the copolymer comprising at least one structural block comprising at least one biologically compatible structural moiety included in its backbone and at least one biologically active block comprising at least one biologically active moiety attached in its backbone,
    wherein the structural moiety comprises units derived from $CH_2=CX—M$ where X is hydrogen or methyl and M is a substituted or unsubstituted aryl group or an ester group $O=C(OR)—$; and where R is an alkyl or aryl group, and
    wherein the biologically active block comprises units derived from a monomer selected from:
    2-acrylamido-2-methyl-1-propanesulfonic acid,
    poly(ethylene glycol) methacrylate,
    3-sulfopropyl acrylate,
    3-sulfopropyl methacrylate, N-vinylpyrrolidone,
acryloyl-, methacryloyl-, or
3-allyloxy-2-hydroxypropanesulfonic acid.

2. The coating of claim 1, wherein the medical device is a stent.

3. The coating of claim 1, wherein the coating additionally includes a therapeutic agent.

4. The coating of claim 1, wherein the biologically active moiety comprises diazenium diolate type nitric oxide donors, polycationic peptides, polysaccharides, pyrrolidone, poly(ethylene glycol), vitamin E, β-phenoxyetanol, N,N-dimethylamino-2-ethanol, or mannose-6-phosphate, sulfonic acid.

5. A coating for an implantable medical device, the coating including a block copolymer, the copolymer comprising at least one structural block comprising at least one biologically compatible structural moiety included in its backbone and at least one biologically active block comprising at least one biologically active moiety attached in its backbone,
wherein the structural moiety comprises units derived from $CH_2=CX-M$ where X is hydrogen or methyl and M is a substituted or unsubstituted aryl group or an ester group $O=C(OR)-$; and where R is an alkyl or aryl group,
wherein the biologically active block comprises units derived from a monomer selected 2-acrylamido-2-methyl-1-propanesulfonic acid, poly(ethylene glycol) methacrylate, 3-sulfopropyl acrylate, 3-sulfopropyl methacrylate, N-vinylpyrrolidone, acryloyl-, methacryloyl-, or 3-allyloxy-2-hydroxypropanesulfonic acid,
wherein the biologically active moiety comprises diazenium diolate type nitric oxide donors, pyrrolidone, poly(ethylene glycol), vitamin E, β-phenoxyetanol, N,N-dimethylamino-2-ethanol, mannose-6-phosphate,
or propanesulfonic acid, 2-methyl-1-propanesulfonic acid, benzenesulfonic acid, or 3-methoxy-2-hydroxypropanesulfonic acid.

6. The coating of claim 1, wherein the block copolymer is selected from a group consisting of AB, ABA, ABC, and ABCBA block copolymers wherein A, B, and C are independent polymer blocks in the copolymer.

7. The coating of claim 1, wherein the block copolymer is made by living free radical copolymerization of plurality of monomers.

8. The coating of claim 7, wherein the monomers forming the structural moiety comprise units derived from $CH_2=CX-M$ where X is hydrogen and M is an ester group $O=C(OR)-$; and where R is an alkyl or aryl group.

9. The coating of claim 7, wherein the monomers forming the structural moiety are selected from a group consisting of methyl methacrylate, n-butyl methacrylate, lauryl methacrylate, 2-hydroxyethyl methacrylate, and styrene.

10. The coating of claim 7, wherein the monomers forming the biologically active moiety include acryloyl-, methacryloyl-, vinyl-, or allyl-modified diazenium diolate type nitric oxide donors.

11. The coating of claim 7, wherein the monomers forming the biologically active moiety are selected from a group consisting of 2-acrylamido-2-methyl-1-propanesulfonic acid, poly(ethylene glycol) methacrylate, 3-sulfopropyl acrylate, 3-sulfopropyl methacrylate, N-vinylpyrrolidone, and 3-allyloxy-2-hydroxypropanesulfonic acid.

12. A method for coating an implantable medical device, the method comprising depositing a block copolymer comprising at least one structural block comprising at least one biologically compatible structural moiety included in its backbone and at least one biologically active block comprising at least one biologically active moiety attached in its backbone onto the device,
wherein $CH_2=CX-M$, where X is hydrogen or methyl and M is a substituted or unsubstituted aryl group or an ester group $O=C(OR)-$; and where R is an alkyl or aryl group, and
wherein the biologically active block comprises units derived from a monomer selected from:
2-acrylamido-2-methyl-1-propanesulfonic acid,
poly(ethylene glycol) methacrylate,
3-sulfopropyl acrylate,
3-sulfopropyl methacrylate,
N-vinylpyrrolidone,
acryloyl-, methacryloyl-, or
3-allyloxy-2-hydroxypropanesulfonic acid.

13. The method of claim 12, wherein the medical device is a stent.

14. The method of claim 12, wherein the copolymer is fabricated by copolymerizing plurality of monomers by a method of living free radical copolymerization.

15. The method of claim 14, wherein the monomers forming the structural moiety comprise units derived from $CH_2=CX-M$ where X is hydrogen and M is an ester group $O=C(OR)-$; and where R is an alkyl or aryl group.

16. The method of claim 14, wherein the monomers forming the structural moiety are selected from a group consisting of methyl methacrylate, n-butyl methacrylate, lauryl methacrylate, 2-hydroxyethyl methacrylate, and styrene.

17. The method of claim 14, wherein the monomers forming the biologically active moiety include acryloyl-, methacryloyl-, vinyl, or allyl-modified diazenium diolate type nitric oxide donors.

18. The method of claim 14, wherein the monomers forming the biologically active moiety are selected from a group consisting of 2-acrylamido-2-methyl-1-propanesulfonic acid, poly(ethylene glycol) methacrylate, 3-sulfopropyl acrylate, 3-sulfopropyl acrylate methacrylate, N-vinylpyrrolidone, and 3-allyloxy-2-hydroxypropanesulfonic acid.

* * * * *